United States Patent
Cho et al.

[11] Patent Number: 5,854,021
[45] Date of Patent: Dec. 29, 1998

[54] ENHANCE PROTEIN PRODUCTION METHOD

[75] Inventors: Myung-Sam Cho, Pinole; Van-Mai Tran, Orinda, both of Calif.

[73] Assignee: Bayer Corporation, Berkeley, Calif.

[21] Appl. No.: 807,415

[22] Filed: Feb. 28, 1997

[51] Int. Cl.[6] .......................... C12N 15/11; C12N 15/63; C12N 15/68; C12N 15/86

[52] U.S. Cl. .................. 435/69.1; 435/172.3; 435/320.1; 536/24.1

[58] Field of Search .............................. 435/320.1, 172.3, 435/69.1; 536/24.1

[56] References Cited

PUBLICATIONS

Baer et al., Nature 310:207–211 (1984).
Jonsson et al., Human Gene Therapy 6:611–623 (1995).

*Primary Examiner*—Johnny F. Railey, II
*Attorney, Agent, or Firm*—Michael J. Beck; James A. Giblin

[57] ABSTRACT

An expression vector comprising a promoter, a coding sequence of a heterologous protein, the coding sequence being operably linked to the promoter, and an intronic sequence downstream of the promoter and upstream of the coding sequence, the intronic sequence comprising two identical donor sites and one acceptor site.

13 Claims, 7 Drawing Sheets

FIG._1a

CGAT [AACTAGCAGCATTTCCTCCAACGAGGATCCCGCAG (GTAAGAA
GCTACACCGGCCAGTGGCCGGGGCCCGATAACTAGCAGCATTTCCTCCAA
CGAGGATCCCGCAG (GTAAGAAGCTACACCGGCCAGTGGCCGGGGCCGTG
GAGCCGGGGGCATCCGGTGCCTGAGACAGAGGTGCTCAAGGCAGTCTCCA
CCTTTTGTCTCCCCTCTGCAG) AGAGCCACATTCTGGAA] GTT

ENHANCE PROTEIN PRODUCTION METHOD

BACKGROUND OF THE INVENTION

1. Field

This invention relates generally to the production of biologically active proteins from genetically-engineered mammalian cell lines. Specifically, the invention is concerned with a novel expression vector containing MIS, a 5'-intronic sequence (5'-IS) derived from Epstein-Barr virus, immediately downstream from a CMV promoter and upstream from the protein coding sequence.

2. Prior Art

Gene amplification is a most commonly used strategy to increase protein production in mammalian cells. For the amplification of a protein coding sequence of interest, a functional transcription unit encoding the protein is normally linked covalently to an amplifiable marker. The expression vector comprising the transcriptional unit and amplifiable marker is then transferred into an appropriate cell, followed by amplification using a drug which allows accompanying selection.

The most widely used gene amplification strategy involves the use of dihydrofolate reductase (dhfr) expression vectors in conjunction with dhfr-deficient Chinese Hamster Ovary (CHO) cells using increasing concentration of methotrexate (MTX) (Kellems, Curr. Opin. Biotechnol. 2:723–729, 1991). A number of commercially valuable proteins including tissue plasminogen activator, erythropoietin, and factor VIII have been produced by this strategy (see U.S. Pat. No. 4,740,461 to Kaufman; and Kaufman, et al., Mol. Cell. Biol. 5: 1750–1759, 1985). Due to the presence of the endogenous dhfr gene, this strategy has generally not been extended to cell hosts that are not dhfr-deficient.

However, successes have also been reported where dhfr-positive cell hosts were used to express therapeutic proteins. U.S. Pat. No. 4,965,199 (Wood et al., 1990) describes a process for producing factor VIII in dhfr-positive Baby Hamster Kidney cells (BHK-21 cells). This process involves (i) the co-transfection of host cells with a DNA sequence coding for factor VIII linked to a dhfr sequence and a selectable marker conferring neomycin resistance, (ii) selection of transfectants in a selective medium containing G418, and (iii) amplification of G418 resistant cells in media containing increasing amounts of methotrexate (MTX).

Walls et al. (Gene, 81: 139–149, 1989) have reported on the use of the dhfr/MTX co-amplification strategy to express functional protein C in human embryonic kidney cells. Okamoto et al. (Biotechnol., 8:550–553, 1990) have also described the amplification and expression of granulocyte stimulating factor (GM-CSF) in human lymphoid cells.

Despite recent advances in recombinant DNA techniques, the derivation of recombinant cell clones with high productivity for factor VIII has remained difficult. Gorman (Eur. pat. appl. no. 0260148, published Sep. 17, 1987; incorporated herein by reference) describes the construction of an expression vector (pCIS-F8) having a stabilizing sequence (an intronic sequence denoted CIS) downstream of a promoter and upstream of the DNA encoding factor VIII. The vector was constructed with a cytomegalovirus (CMV) promoter and enhancer, a cDNA encoding factor VIII, and a 3' terminating sequence. In the absence of this stabilizing sequence, expression of factor VIII was not observed in any cell types tested. This stabilizing sequence was also linked to a DNA sequence encoding prorelaxin. Secretion of both proteins in a transient transfection assay was dependent on the presence of the stabilizing sequence.

Stolzenburg et al. (Chromosoma, 103:209–214, 1994) observed that the 180 bp homology region of muNTS2 was essential for the amplification promoting activity in mammalian cells. However, stable gene expression using this sequence was not known.

I have now found that by using a novel expression vector constructed using available technology it is now possible to increase protein expression significantly. Details of the vector and how to make and use it are described below.

SUMMARY OF INVENTION

The expression vector described herein comprises a CMV promoter and enhancer, an intronic sequence having two identical donor sites followed by a single acceptor site, an unique restriction enzyme site (HpaI) to insert a reporter gene, and a poly-A region followed by a selection marker and a plasmid backbone. In a preferred embodiment the intronic sequence is derived from Ebstein-Barr virus and is denoted MIS. This vector is denoted pSM97. This vector is used to introduce the reporter gene, i.e. the appropriate DNA coding sequence for a desired protein, into mammalian cells to increase protein expression by the cells and to stabilize expression of the protein in a long term culture. In one preferred embodiment the sequence of the reporter gene codes for soluble tICAM-1(453) (see Grove et al., J. Virol. 65:6015–6023, 1991). The resulting vector is pSM98.

Surprisingly, expression vectors incorporating an upstream (5') intronic sequence, e.g. MIS, showed increased amplification of the expression vector in dhfr/MTX system, when compared to the amplification of a vector without the 5'-IS. The efficient amplification of the vector enabled greater stable expression of the reporter gene product, e.g. soluble tICAM-1(453).

A preferred amplifiable marker is dihydrofolate reductase (dhfr) although other markers such as glutamine synthetase (GS) and multidrug-resistance gene (mdr) can be substituted. The cell host to be transfected can be any mammalian cell and need not be dhfr-deficient. Cell lines that are known to integrate selection genes into their chromosomal DNA are optimal; for example, human embryonic kidney (293S), human B-cell, chinese hamster ovary (CHO), baby hamster kidney (BHK-21), and mouse myeloma cell lines.

Secretion of tICAM-1(453) from the cells transfected with the vectors with or without a 5'-IS was almost the same in transient transfection assays and even early during the amplification process. However, tICAM-1(453) secretion from individual clones (after gene amplification using MTX) derived from the vector pSM98 was higher and more stable than those clones derived from the vector pSH92, which lacks the 5'-IS sequence. The high secreting cell lines contained higher integrated vector copy number of tICAM-1(453) coding sequence (higher than 20 copies per cell, estimated from Southern analysis) from the vector with a 5'-IS. On the other hand, cell lines derived from vectors without a 5'-IS were unstable in long term culture and contained lower integrated vector copy number of tICAM-1(453) (a few copies per cell, estimated from Southern analysis). Therefore, the productivity of a transfected mammalian cell line can be enhanced and stabilized using the vector containing 5'-IS.

SPECIFIC EMBODIMENTS

Construction of Expression Vectors

Figure 1A:
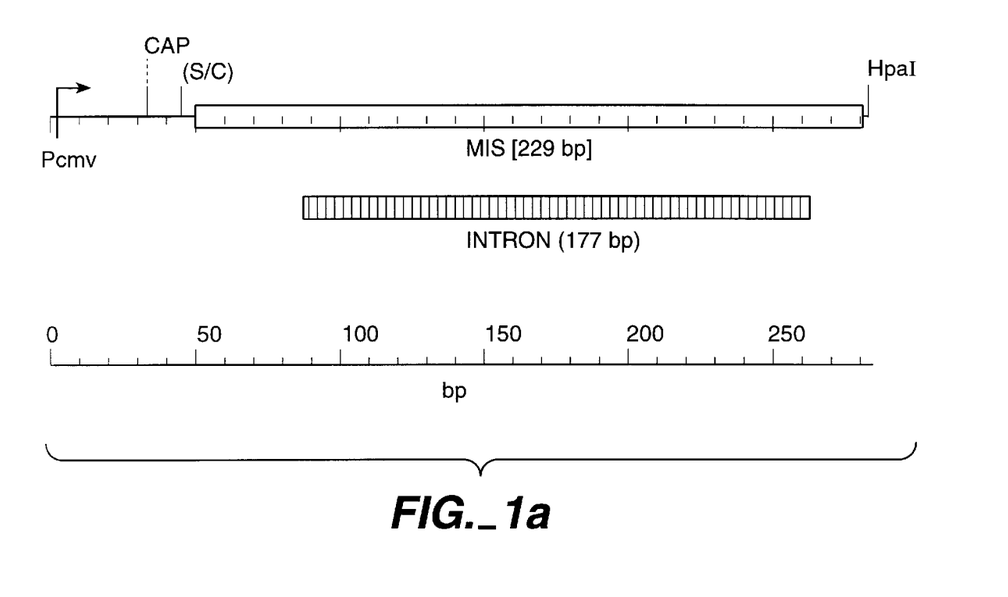
FIG. 1a shows a linear map of the CMV promoter, a 5'-intronic sequence (MIS), and HpaI cloning site. The parallel map shows the location of the 177 bp intron within the MIS sequence.
Figure 1B:
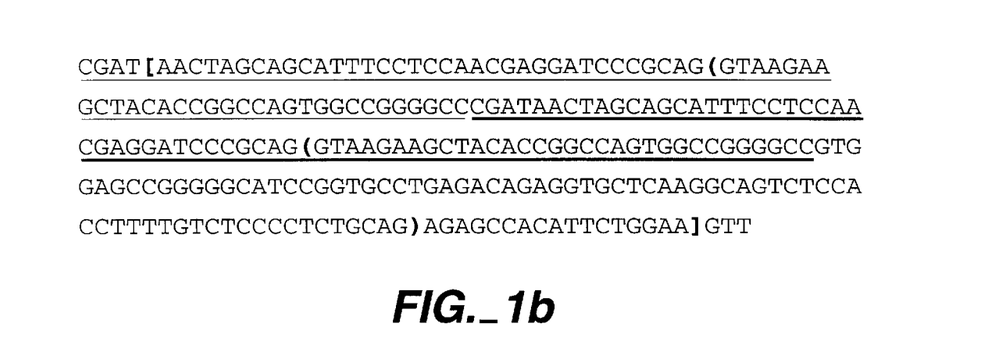
FIG. 1b shows the nucleotide sequence of MIS in pSM98. Denoted are the nucleotide sequence derived from EBV (bracketed, 229 bp, SEQ ID NO: 1) and its two donor-site (open-parenthesis signal) and one acceptor-site (close-parenthesis signal). Two repeated sequences (2×71 bp) are underlined (thin and thick). (The entire sequence listed in the figure is SEQ ID NO: 4).
Figure 2:
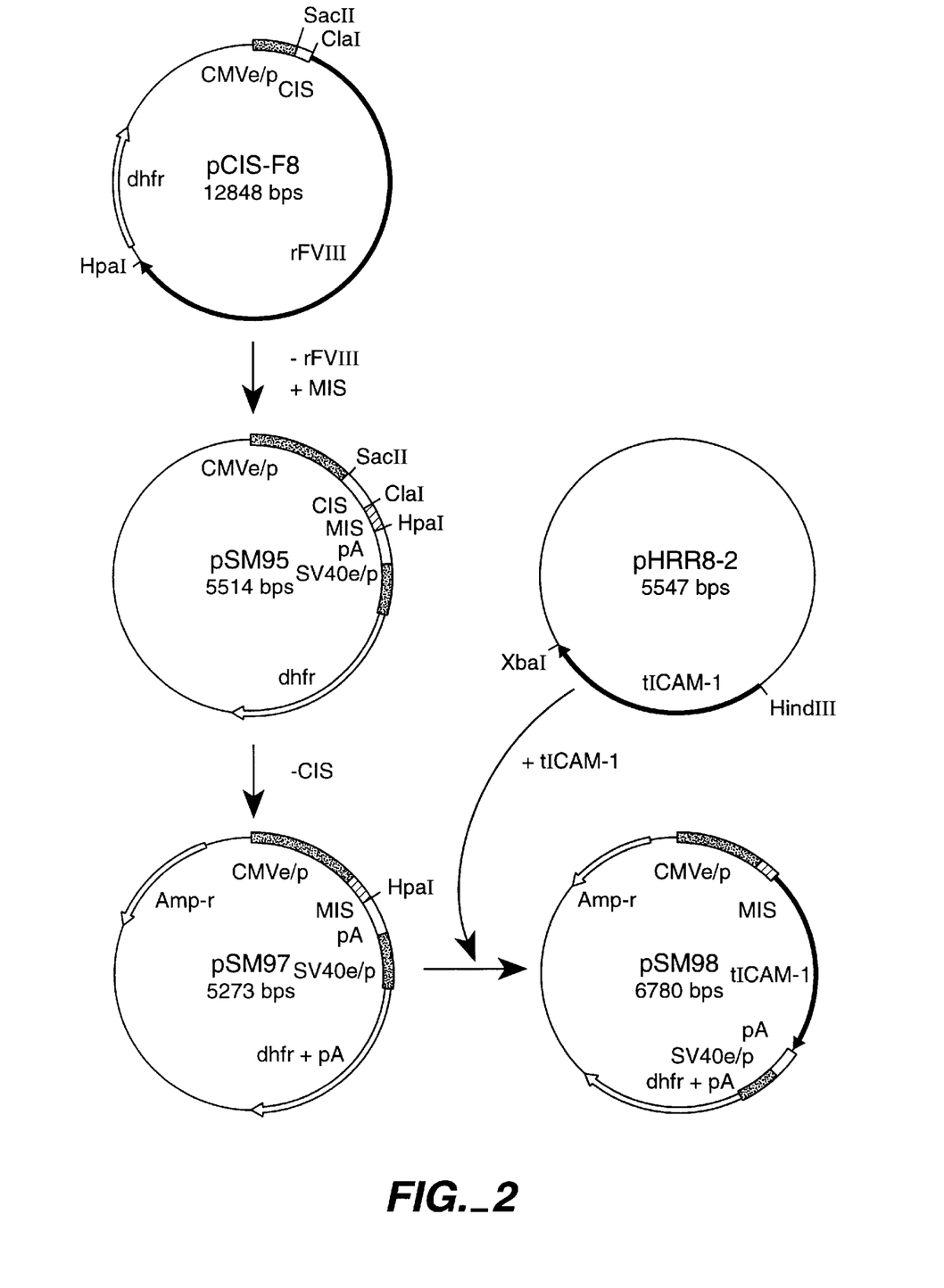
FIG. 2 shows a flow chart illustrating the construction scheme of the vector pSM98.

The MIS sequence was made by polymerase chain reaction (PCR) from an Epstein-Barr virus (EBV) reading frame designated BMLF1. This MIS sequence encompasses DNA sequence from 84,105 to 84,262 of B95-8 Epstein-Barr virus encluding an intronic sequence from 84,122 to 84,227 of B95-8 EBV (Farrell, Advances in Viral Oncology, vol. 8, edited by G. Klein, Raven Press, Ltd., New York, 1989; Genbank Access # X00784). Two primers (5'GGATCGATAACTAGCAGCATTTCCT3' (SEQ ID NO:2) and 5'GGGTTAACTTCCAGAATGTGGCTCT3' (SEQ ID NO:3) ) have extended restriction enzyme sites of ClaI (ATCGAT) and HpaI (GTTAAC) sequences at the 5'- and 3'-ends of the fragment (MIS) for directional cloning, respectively. For the PCR amplification, the protocol described in the AmpliTaq DNA polymerase kit (Perkin Elmer Cetus #N8008-0070) was used and the reaction was run in the DNA Thermal Cycler (Perkin Elmer Cetus #N801-0150). The $MgCl_2$ concentration in the PCR reaction mix was varied from 1.5 mM to 4.0 mM. Denaturation of the template DNA took place at 95° C., for ten minutes. The amplification cycle was started with the initial melting step at 95° C. for one minute followed by the annealing step at 60° C. for one minute and by the extension step at 72° C. for one minute. This cycle was repeated 30 times, and the reaction was stopped and soaked at 4° C. overnight. The PCR amplified fragment was digested with HpaI and ClaI and then inserted into the ClaI and HpaI sites of pCIS-F8 (after first removing the factor VIII sequence). The resulting plasmid containing MIS was referred to as pSM95. See FIG. 2. This MIS sequence is different from the original EBV sequence by having an unexpected repeat of a 71 bp sequence which contains a donor site. Therefore, the MIS sequence (229 bp) has two donor-sites and one acceptor-site (see FIG. 1).

Figure 3:
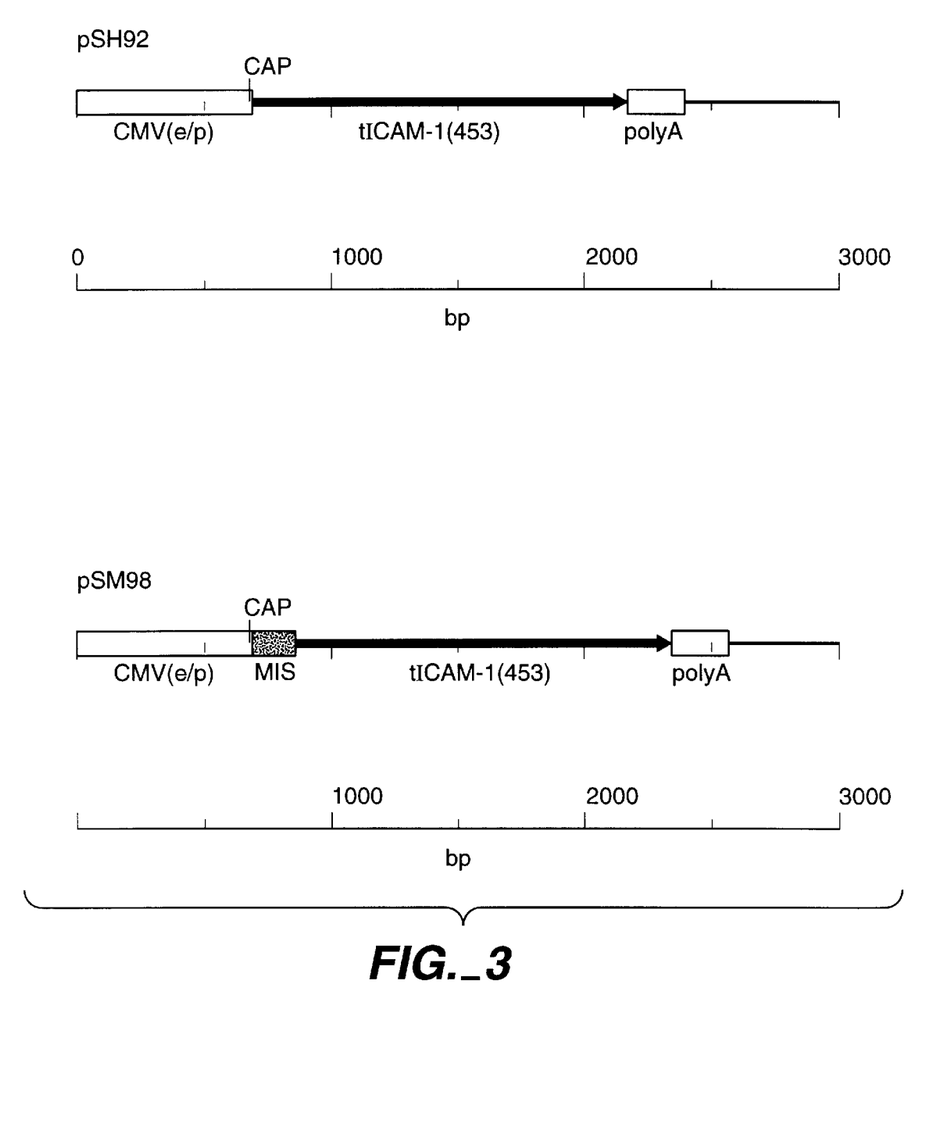
FIG. 3 shows linear maps of the first 3,000 bp from the plasmids pSH92 and pSM98. The expression vector pSH92 contains a blunt ended tICAM-1(453) coding sequence (a solid arrow) at the 3' end of CMV promoter. pSM98 harbors a 5'-intronic sequence, MIS (a hatched box), at the 5'-end of the untranslated tICAM-1(453) coding sequence (a solid arrow).

Subsequently, the intronic sequence CIS was removed from pSM95 by SacII and ClaI digestion. The remaining backbone was blunt ended by Klenow and religated. This resulting plasmid, pSM97, consists of a CMV promoter/enhancer (CMVe/p), MIS, a unique HpaI site for cloning, a poly A signal, and a SV40 early promoter-dhfr in a plasmid backbone containing ori and $amp^r$ gene. tICAM-1(453) coding sequence, which was prepared from pHRR8-2 (Greve, J. M. et al., J. Virol. 65: 6015–6023, 1991) by digestion with HindIII and XbaI, was blunt ended and inserted into the HpaI site of pSM97. The correct orientation of tICAM-1(453) in pSM97 was referred to as pSM98 (FIG. 2). pSH92 is the same as pSM98 except missing the MIS sequence (FIG. 3). Plasmid DNA was prepared by methods described in Molecular Cloning (edited by Maniatis et al., 86–94, 1982).

ELISA Assay to Measure tICAM1(453)

A monoclonal antibody to ICAM-1, C92.5 (McClelland et al., Proc. Natl. Acad. Sci. USA 88: 7993–7997, 1991) was adsorbed onto round bottom microtiter plates. The plates were blocked by treatment with a solution of PBS containing 1% BSA, then incubated with tICAM-1(453) containing samples. Plates were then washed with washing buffer (PBS plus 0.005% Tween 20) and incubated with biotinylated C78.5, a second monoclonal antibody to a different epitope on tICAM-1(453) (McClelland et al., 1991, supra). After washing, the plates were incubated with HRP-streptavidin. The plates were then washed with washing buffer, reacted with tetramethyl benzidine (TMB), and the reaction was stopped with 1N HCl. The tICAM-1(453) concentration was determined by reading the OD at 450/570 nm and comparing to a standard curve of purified tICAM-1(453).

Transient Transfection Assays to Test Expression Vectors

To test the biological activity of the expression vectors, 293S cells were transfected with the vectors pSH92 and pSM98. In each experiment, the same number of cells (~2×10$^6$ cells/well) were mixed with 3 μg of each vector DNA preincubated with cationic liposome DMRIE-C (Life Technologies, #10459-014) according to the provided protocol from Life Technologies. Vector DNA concentration was carefully determined using a DNA fluorometer (Hoefer Science Instruments, Model TKO 100) and confirmed by agarose gel. After a five hour incubation of the cells with the cocktail (1 ml) of DNA and DMRIE-C, fresh medium supplemented with 5% FBS was added to the well. Cell numbers were counted at two to three days after transfection. The level of tICAM-1(453) secretion was determined by ELISA. From the repeated transient transfection assays, we observed that there is no apparent difference of tICAM-1(453) secretion from the 293S populations transfected with the two different vectors (with or without 5'-intronic sequences (5'-IS)). See Table 1. These results indicate that the 5'-IS in pSM98 has no direct influence on expression of tICAM-1(453) in transient transfection assays. This observation is different from the Gorman patent, which showed stabilizing effect on the expression of certain proteins in transient transfection assays.

TABLE 1

Comparison of tICAM-1(453) expression in transient transfection assay using expression vectors with and without 5'-IS, pSM98 and pSH92, respectively.

| | 293S (μg/10$^6$ cells/3 d) | | |
|---|---|---|---|
| | Exp. I | Exp. II | Exp. III |
| pSH92 | 1.9 | 3.3 | 1.8 |
| pSM98 | 1.1 | 1.5 | 1.7 |

Figure 4:
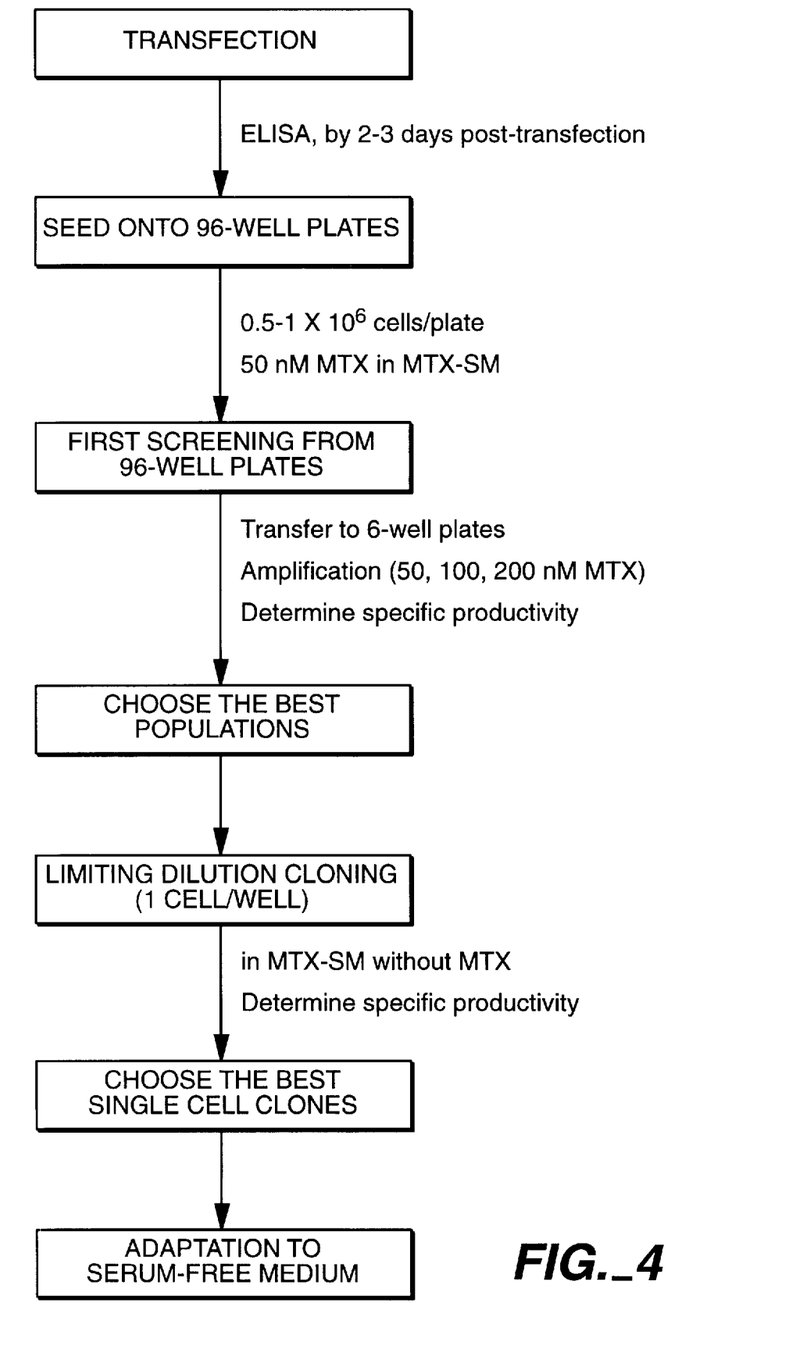
FIG. 4 shows a flow chart illustrating the overall process of deriving clones which secrete tICAM1(453).

Production cell lines were established by transfection of 5–10×10$^6$ cells with 10 μg of expression vectors, pSH92 and pSM98, mainly, by electroporation using a Transfector 300 (BTX) set at 715 V/cm and 300 μF. Transfected cells were cultured in 18 ml of medium supplemented with 10% fetal bovine serum (FBS) in a 6-well (3 ml per well) format. Two to three days after transfection, ELISA assays were performed to check transfection efficiency. About 10$^6$ cells per 96-well format (200 μl/well) were cultured in the methotrexate (50 nM) containing selection medium consisting of Dulbecco's modified Eagle medium and nutrient mixture F-12 (1:1) lacking hypoxanthine and thymidine, supplemented with 10% dialyzed FBS. This methotrexate-containing selection medium was called MTX-SM. One half of the medium in each well (100 μl) was exchanged with fresh MTX-SM weekly.

tICAM-1(453) productivity was determined by ELISA from the 96-well plates at 3 weeks post transfection. The cells of the highest signaling wells in the 96-well formats were transferred to 6-well format. After repeated determination of the productivity, the best secreting initial populations, usually 4–6 populations, were further treated with increasing concentration of MTX (50, 100, and 200 nM) to amplify the expression vector. To obtain single cell clones, limiting dilution cloning (LDC) was applied using 96-well formats (0.5–2 cell/well) at the stage of 100 nM and 200 nM MTX. One week and two weeks after seeding the cells, the 96-well plates were tested under microscope to check single cell growth in each well. During the LDC and thereafter, MTX was omitted from the selection medium, but 10% dialyzed FBS was included. Productivity was determined by ELISA at about two weeks post-seeding. Cells of the highest secreting wells grown from single cells were transferred to 6-well formats and specific productivity (pg/cell/day) was measured repeatedly to choose clones secreting the highest levels of tICAM-1(453). The adaptation of the best performing clones (4–6 clones) into serum-free medium was performed by gradual reduction of the serum content in culture medium using T75 tissue culture bottles. See FIG. 4 for a summary of the process of deriving clones which show high productivity. We have observed that the clones derived from pSH92 showed production instability throughout the increased amplification steps.

Integrated Genomic Copy Numbers in tICAM-1(453) Secreting Clones

The integrated vector copy number per cell was determined from the Southern blot hybridization probed with a fragment (663 bp) of tICAM-1(453) coding sequence, which was prepared by polymerase chain reaction. Southern analysis was done as described in the Amersham protocol, basically according to Southern (J. Mol. Biol., 98: 503–517, 1975) and Wahl et al., (Proc. Natl. Acad. Sci. USA, 76: 3683–3687, 1979), using cellular DNA made from individual clones. To prepare total cell DNA cells in logarithmic growth phase were collected and washed twice with phosphate buffered saline (PBS). The pellet was resuspended in a small volume of PBS/lysis buffer (2:1). The lysis buffer consisted of 3% sarkosyl, 75 mM Tris, pH 8 and 25 mM EDTA. After incubation at 37° C. for 60 minutes with DNase-free RNase (final concentration of 100 μg/ml), proteinase K (final concentration of 200 μg/ml) was added and incubation was continued at 50° C. overnight. An equal volume of phenol saturated with 0.1M Tris, pH 8, was added and the suspension was gently mixed. The DNA containing aqueous phase was separated from the organic phase after centrifugation. Phenol treatment was repeated until a clean interphase was observed, followed by a similar extraction with chloroform (two to three times). The DNA in the aqueous phase was precipitated by adding two volumes of cold absolute ethanol and mixing slowly. The white precipitated DNA was spooled using a sealed pasteur pipet. After complete drying of alcohol, DNA was resuspended in a small volume of 10 mM Tris, pH 8, 1 mM EDTA. DNA concentration was determined by measuring absorbance at 260 and 280 nm.

Figure 5A:
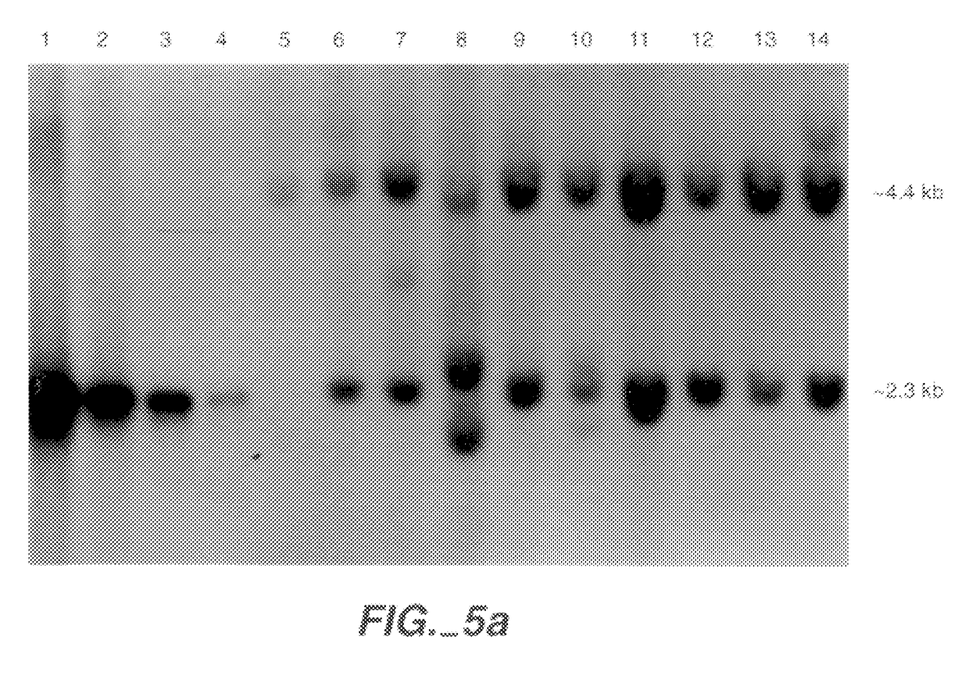
FIG. 5a shows Southern blot hybridization of tICAM-1 (453) secreting clones derived from 293 S cells transfected with pSH92. Each lane indicates as follows;
1. Standard plasmid DNA equivalent to 50 genome copy per cell
2. Standard plasmid DNA equivalent to 20 genome copy per cell
3. Standard plasmid DNA equivalent to 5 genome copy per cell
4. Standard plasmid DNA equivalent to 1 genome copy per cell
5. 293S cellular DNA
6 to 14: cellular DNAs prepared from nine tICAM-1(453) secreting clones derived from 293S cells transfected with pSH92
Figure 5B:
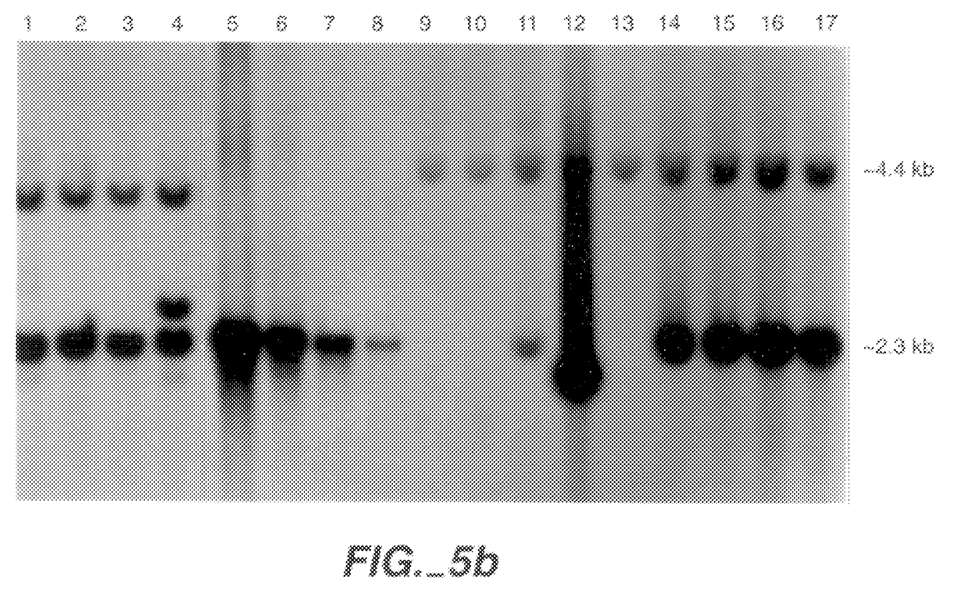
FIG. 5b shows Southern blot hybridization of tICAM-1 (453) secreting clones derived from 293S cells transfected either with pSH92 or with pSM98. Each lane indicates as follows;
1 to 4: Cellular DNAs prepared from four tICAM-1(453) secreting clones derived from 293S cells transfected with pSM98
5: Standard plasmid DNA equivalent to 50 genome copy per cell
6: Standard plasmid DNA equivalent to 20 genome copy per cell
7: Standard plasmid DNA equivalent to 5 genome copy per cell
8: Standard plasmid DNA equivalent to 1 genome copy per cell
9: 293S cellular DNA
10 to 13: Cellular DNAs prepared from tICAM-1(453) secreting clones derived from 293S cells transfected with pSH92
14 to 17: Cellular DNAs prepared from tICAM-1(453) secreting clones derived from 293S cells transfected with pSM98.

To determine integrated genomic copy numbers, EcoRI digested pSM98 DNA equivalent to 1, 5, 20, and 50 genome per cell was loaded on the gel together with cell DNA. An internal control of 4.4 kb derived from the endogenous ICAM-1 gene equivalent to 2–3 copies per cell provided an excellent condition to determine low copy numbers (3 copies in the case of 293S cells, which have a haplotriploid chromosome number). The protected size of tICAM-1(453) coding sequence in Southern analysis was 2.3 kb after digestion of the expression vectors with EcoRI, including complete CMV enhancer/promoter, MIS, and complete tICAM-1(453) coding sequence. The integrated tICAM-1(453) (2.3 kb size) coding sequence copy number per cell in most of the clones derived from the vector pSH92 was similar with endogenous (4.4 kb size) ICAM-1 copy number per cell of 293S clones (FIG. 5a and 5b). However, the clones derived from 293S and CHO cells transfected with pSM98 contained higher integrated vector copy number (20–40) per cell (FIG. 5b, FIG. 6).

Comparison of Specific Productivity and Integrated Vector Copy Numbers per Cell

Figure 6:
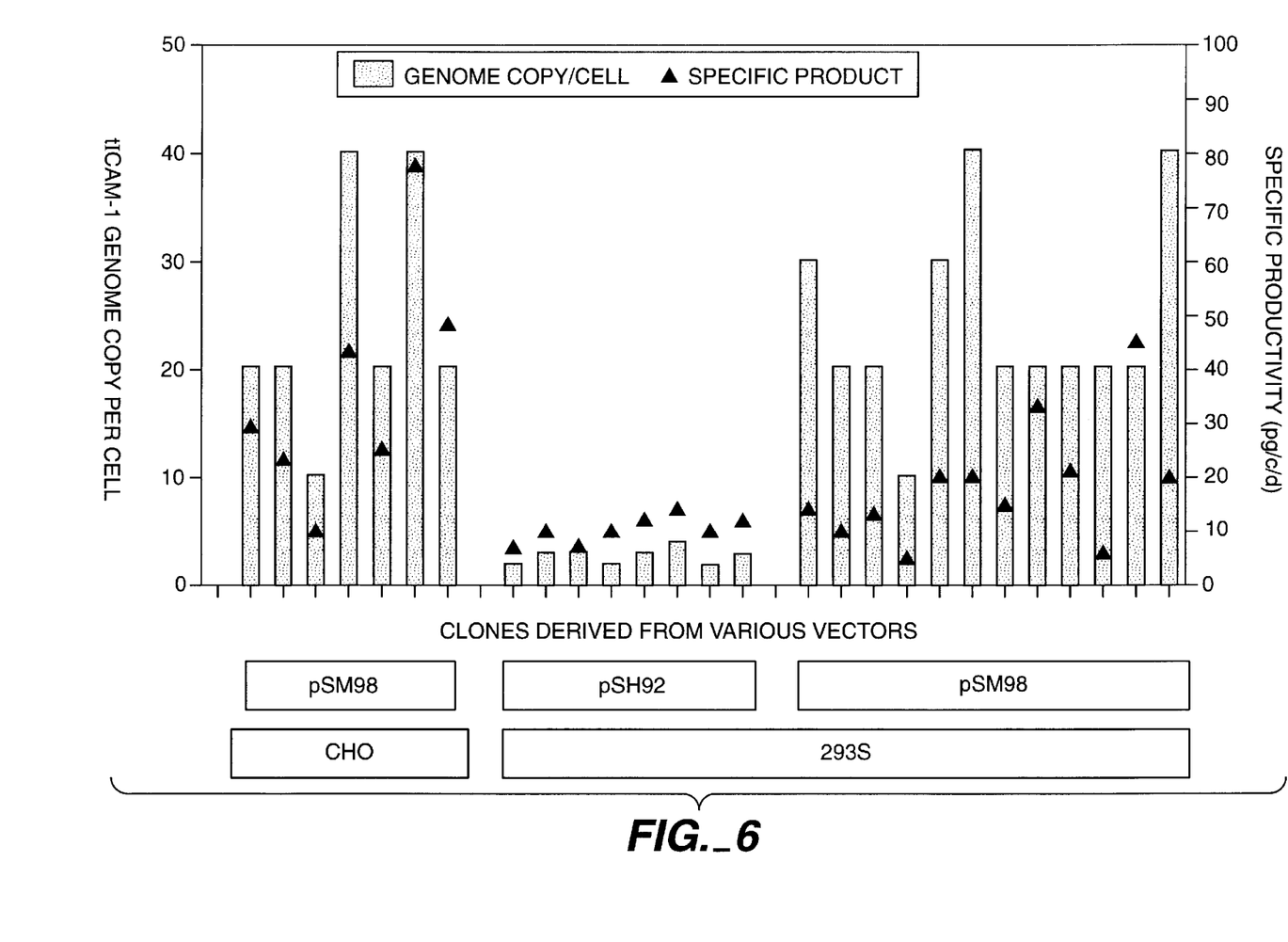
FIG. 6 compares the integrated copy number estimated from Southern analysis and the productivity of clones determined by ELISA. An individual clone was derived either from CHO cells (CHO) or from 293S cells (293S) which were transfected using either the vector with a 5'-intronic sequence (pSM98) or the vector without a 5'-intronic sequence (pSH92).

A significant correlation was observed between two groups of clones (FIG. 6). One group of clones, those derived from expression vectors with 5'-IS, showed high productivity (~20 pg/c/d) with a high integrated vector copy number (~20 copies/cell). The other group of clones, those derived from a vector lacking a 5'-IS in the untranslated region of the ICAM-1 coding sequence, secreted lower levels of tICAM-1(453) (1–10 pg/c/d) and contained lower integrated vector copy numbers (2–3 copies/cell). The latter group were not stable producers; specific productivity decreased during long term culture, and it was very difficult or impossible to recover original productivity from the frozen/thawed cells. These results indicate that the intronic sequence located in the 5'-untranslated region of a protein coding sequence enhances the amplification of the expression vector DNA in dhfr/MTX amplification system. This is a surprising new observation of the function of 5'-IS in addition to the previous observation of the mRNA stabilizing function (Huang and Gorman, Nucleic Acid Research 18: 937–946, 1990).

EXAMPLE

Continuous Production of tICAM-1(453)

Clone 4H9-23 (derived from 293S cells transfected with pSM98) was adapted to serum-free medium and was maintained for more than one year in the serum free medium MICT4.1 without decreasing productivity. During this period we have frozen the cells at 6 weeks, 3 months, and 8 months after adaptation in SFM. tICAM-1 productivity was determined from the maintained culture and from the frozen/thawed cells and was observed to be stable with specific productivity of ~20 pg/c/d and daily titer of 80–100 μg/ml. Three CHO clones derived from pSM98 (B9-H12, B9-H12-G11, and B9-E10) were adapted to serum free medium. All three clones were stable more than 5 months in serum free medium without a decrease in productivity (10–20 pg/c/d). A 293S clone (4H9-23) and a CHO clone (B9-E10) were maintained in bioreactors with continuous perfusion. 4H9-23 cells, which were thawed from the frozen ampule after 3 months culture, showed maximum productivity of 300 mg/l/d (volumetric productivity) in MICT4.1 supplemented with 2 g/l of human serum albumin, 10 μg/l of insulin, and 11 μg/l of transferrin during a 10 week long study. B9-E10 showed a volumetric productivity of 400–500 mg/l/d using the same medium without human serum albumin during a 100 day-study. Detailed fermenter data are not shown.

CONCLUSION

A novel mammalian cell expression vector for introducing a DNA coding sequence for a protein into mammalian cell lines was developed to increase stable protein expression. The vector comprises an intronic sequence (IS) derived from Epstein-Barr virus immediately downstream from a CMV promoter and an unique cloning site (HpaI) with poly A region. The expression vector shows improved amplification efficiency in transfected cells and aids in deriving high producing stable cell clones. The vector is especially useful for increased and stable production of tICAM-1(453) in several host mammalian cells.

It is recognized that, given the above examples, variations will be readily apparent to those skilled in the art. Accordingly, it is intended that the above examples should be construed as illustrative only and that the invention should be limited only by the following claims.

What is claimed is:

1. An expression vector comprising
   a) a promoter,
   b) a coding sequence of a heterologous protein, the coding sequence being operably linked to the promoter, and
   c) a MIS sequence, the MIS sequence being downstream of the promoter and upstream of the coding sequence.

2. The expression vector of claim 1, wherein the vector further comprises an amplifiable marker.

3. The expression vector of claim 2, wherein the amplifiable marker is selected from the group consisting of dihydrofolate reductase, glutamine synthetase, and multidrug-resistance gene.

4. The expression vector of claim 1, wherein the coding sequence codes for a protein having biological activity substantially equivalent to tICAM1(453).

5. The expression vector of claim 1, wherein the coding sequence codes for tICAM1(453).

6. A DNA molecule comprising the following DNA sequence:

AACTAGCAGC ATTTCCTCCA ACGAGGATCC CGCAGGTAAG AAGCTACACC

GGCCAGTGGC CGGGGCCCGA TAACTAGCAG CATTTCCTCC AACGAGGATC

CCGCAGGTAA GAAGCTACAC CGGCCAGTGG CCGGGGCCGT GGAGCCGGGG

GCATCCGGTG CCTGAGACAG AGGTGCTCAA GGCAGTCTCC ACCTTTGTC

TCCCCTCTGC AGAGAGCCAC ATTCTGGAA   (SEQ ID NO: 1)

7. An isolated DNA molecule according to claim 6.

8. A method of increasing stable protein expression of mammalian cell lines comprising the steps of
   a) transfecting a population of mammalian cells with an expression vector comprising an amplifiable marker and a MIS sequence,
   b) growing the cells in the presence of an amplifying agent, and
   c) selecting at least one cell line having high productivity from the cells of step b.

9. The method of 8, wherein the mammalian cells are selected from the group consisting of human embryonic kidney cells, human B-cells, chinese hamster ovary cells, baby hamster kidney cells, mouse myeloma cells, cells derived from human embryonic kidney cells, cells derived from human B-cells, cells derived from chinese hamster ovary cells, cells derived from baby hamster kidney cells, and cells derived from mouse myeloma cells.

10. A method of increasing the number of copies of DNA from a vector integrated into a cell's chromosomal DNA, the method comprising a) transfecting a population of cells with an expression vector having a promoter, a coding sequence, and a MIS sequence located between the promoter and coding sequence, the expression vector further comprising an amplifiable marker, b) growing the cells in the presence of an amplifying agent, and c) selecting at least one cell from the cells of step b having an increased number of vector DNA copies integrated into chromosomal DNA.

11. The method of claim 10, wherein the mammalian cells are selected from the group consisting of human embryonic kidney cells, human B-cells, chinese hamster ovary cells, baby hamster kidney cells, mouse myeloma cells, cells derived from human embryonic kidney cells, cells derived from human B-cells, cells derived from chinese hamster ovary cells, cells derived from baby hamster kidney cells, and cells derived from mouse myeloma cells.

12. The method of claim 10, wherein the coding sequence codes for a protein having biological activity substantially equivalent to tICAM1(453).

13. The method of claim 10, wherein the coding sequence codes for tCIAM1(453).

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
    ( A ) LENGTH: 229
    ( B ) TYPE: nucleic acid
    ( C ) STRANDEDNESS: single
    ( D ) TOPOLOGY: linear   ( x i ) SEQUENCE DESCRIPTION: SEQ ID NO: 1:

| | | | | | |
|---|---|---|---|---|---|
| AACTAGCAGC | ATTTCCTCCA | ACGAGGATCC | CGCAGGTAAG | AAGCTACACC | 50 |
| GGCCAGTGGC | CGGGGCCCGA | TAACTAGCAG | CATTTCCTCC | AACGAGGATC | 100 |
| CCGCAGGTAA | GAAGCTACAC | CGGCCAGTGG | CCGGGGCCGT | GGAGCCGGGG | 150 |
| GCATCCGGTG | CCTGAGACAG | AGGTGCTCAA | GGCAGTCTCC | ACCTTTTGTC | 200 |
| TCCCCTCTGC | AGAGAGCCAC | ATTCTGGAA | | | 229 |

( 2 ) INFORMATION FOR SEQ ID NO: 2:

( i ) SEQUENCE CHARACTERISTICS:
    ( A ) LENGTH: 25
    ( B ) TYPE: nucleic acid
    ( C ) STRANDEDNESS: single
    ( D ) TOPOLOGY: linear   ( x i ) SEQUENCE DESCRIPTION: SEQ ID NO: 2:

-continued

```
GGATCGATAA CTAGCAGCAT TTCCT                                                    25
```

( 2 ) INFORMATION FOR SEQ ID NO: 3:

( i ) SEQUENCE CHARACTERISTICS:
        ( A ) LENGTH: 25
        ( B ) TYPE: nucleic acid
        ( C ) STRANDEDNESS: single
        ( D ) TOPOLOGY: linear     ( x i ) SEQUENCE DESCRIPTION: SEQ ID NO: 3:

```
GGGTTAACTT CCAGAATGTG GCTCT                                                    25
```

( 2 ) INFORMATION FOR SEQ ID NO: 4:

( i ) SEQUENCE CHARACTERISTICS:
        ( A ) LENGTH: 236
        ( B ) TYPE: nucleic acid
        ( C ) STRANDEDNESS: single
        ( D ) TOPOLOGY: linear     ( x i ) SEQUENCE DESCRIPTION: SEQ ID NO: 4:

```
CGATAACTAG CAGCATTTCC TCCAACGAGG ATCCCGCAGG TAAGAAGCTA                          50

CACCGGCCAG TGGCCGGGGC CCGATAACTA GCAGCATTTC CTCCAACGAG                         100

GATCCCGCAG GTAAGAAGCT ACACCGGCCA GTGGCCGGGG CCGTGGAGCC                         150

GGGGGCATCC GGTGCCTGAG ACAGAGGTGC TCAAGGCAGT CTCCACCTTT                         200

TGTCTCCCCT CTGCAGAGAG CCACATTCTG GAAGTT                                        236
```